United States Patent [19]

Huff et al.

[11] 4,064,243

[45] Dec. 20, 1977

[54] HETEROCYCLIC-SUBSTITUTED 1,3,5-OXADIAZIN-2-ONE COMPOUNDS USEFUL FOR COMBATTING COCCIDIOSIS

[75] Inventors: Roger K. Huff, Wokingham, England; Jean Jacques Gallay, Magden; Manfred Kühne, Pfeffingen, both of Switzerland

[73] Assignee: Ciba-Geigy Corporation, Ardsley, N.Y.

[21] Appl. No.: 689,884

[22] Filed: May 25, 1976

[30] Foreign Application Priority Data

June 2, 1975  Switzerland ................... 7104/75
Apr. 1, 1976  Switzerland ................... 4065/76

[51] Int. Cl.$^2$ ............... A01N 9/00; A01N 9/22; C07D 265/00; C07D 273/00; A61K 31/535
[52] U.S. Cl. .................. 424/248.5; 424/248.51; 424/248.53; 424/248.52; 424/248.54; 424/248.55; 424/248.56; 424/248.57; 424/248.58; 544/67
[58] Field of Search ............... 260/244 R; 424/248.4, 424/248.51, 248.53; 248.57, 248.56

[56] References Cited

U.S. PATENT DOCUMENTS

| | | | |
|---|---|---|---|
| 3,136,763 | 6/1964 | Eisenbraun | 260/244 |
| 3,294,793 | 12/1966 | Seidel | 260/244 |
| 3,468,884 | 9/1969 | Crovetti et al. | 260/244 |
| 3,829,419 | 8/1974 | Weir | 260/244 |
| 3,833,577 | 9/1974 | Lin | 260/244 |
| 3,966,721 | 6/1976 | Huff | 260/244 |

OTHER PUBLICATIONS

Chem. Abst. 83 193,245(d)-(1975)-Gompper et al., "4,6-Bis[dialkylamino]-2 oxo-2H-1,3,5 oxadiazines".

*Primary Examiner*—Albert T. Meyers
*Assistant Examiner*—D. W. Robinson
*Attorney, Agent, or Firm*—Harry Falber

[57] ABSTRACT

New diazine derivatives corresponding to the formula

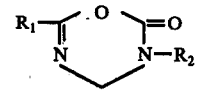

wherein $R_1$ denotes a heterocyclic-aromatic radical which is optionally substituted by halogen, lower alkyl, aryl, nitro, cyano, trifluoromethyl, carboxyl, $R_3OOC—$, $(R_3)_2NCO—$, $(R_3)_2N—$, $R_3O—$, $R_3SO_2—$, $R_3SO—$ or $R_3S—$, and $R_2$ and $R_3$ independently of one another denote lower alkyl, alkoxyalkyl, alkenyl or cycloalkyl which is optionally bonded via an alkylene bridge, processes for the production of the new compounds, compositions containing these compounds and a process for combating Coccidia.

7 Claims, No Drawings

HETEROCYCLIC-SUBSTITUTED 1,3,5-OXADIAZIN-2-ONE COMPOUNDS USEFUL FOR COMBATTING COCCIDIOSIS

The present invention relates to new diazine derivatives and a process for their manufacture and also to agents and a process for combating Coccidia.

The new diazine derivatives correspond to the following formula I

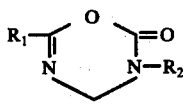
(I)

In this formula $R_1$ denotes a heterocyclic-aromatic radical which is optionally substituted by halogen, lower alkyl, aryl, nitro, cyano, trifluoromethyl, carboxyl, $R_3OOC-$, $(R_3)_2NCO-$, $(R_3)_2N-$, $R_3O-$, $R_3SO_2-$, $R_3SO-$ or $R_3S-$, and $R_2$ and $R_3$ independently of one another denote lower alkyl, alkoxyalkyl, alkenyl or cycloalkyl which is optionally bonded via an alkylene bridge.

In the formula I lower alkyl is understood as straight-chain or branched radicals with 1 to 6 carbon atoms and preferably with 1 to 4 carbon atoms, such as, for example, the methyl, ethyl, n-propyl, isopropyl, n-butyl, isobutyl, sec.-butyl or tert.-butyl radical as well as n-pentyl or n-hexyl and the isomers thereof. Alkenyl radicals contain 2-6, preferably 3-4, carbon atoms, such as, for example, allyl or methallyl. Alkoxyalkyl radicals contain a total of up to 8 carbon atoms. Cycloalkyl radicals contain 3 to 6 carbon atoms and can be bonded via a methylene or ethylene bridge and also can optionally carry methyl or ethyl as substituents. Heterocyclic-aromatic radicals are to be understood as 5-membered to 7-membered, preferably 5-membered to 6-membered, ring systems which contain N, S or O and, optionally, fused benzene rings. Examples of possible radicals are: pyrazinyl, pyrrolyl, thiazolyl, imidazolyl, pyrimidinyl, furyl, thienyl, pyridinyl, quinolyl, indolyl and benzofuranyl radicals. Heterocyclic structures containing nitrogen can be in the form of their quaternary ammonium compounds or N-oxides.

The new diazine derivatives of the formula I are obtained when an amide of the formula II

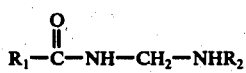
(II)

in which $R_1$ and $R_2$ possess the meaning indicated under formula I, is cyclized with a compound of the formula III

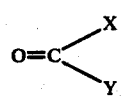
(III)

in which X or Y independently of one another represent chlorine or the radicals $-OR'$ or

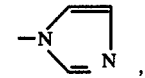

$R'$ denoting an alkyl radical with 1 to 2 carbon atoms.

The cyclization is carried out by reacting the amide of the formula II at temperatures between $-50°$ C and $+30°$ with a compound of the formula III in the presence of a base in solvents and/or diluents which are inert towards the reactants and subsequently carrying out cyclisation in the presence of a base at temperatures between $-15°$ and $120°$ and, if desired, also under pressure.

Solvents or diluents which can be used are aliphatic or aromatic hydrocarbons, such as benzene, toluene, xylenes or hexane; halogenated hydrocarbons, such as chloroform or methylene chloride; ketones, such as acetone or methyl ethyl ketone; nitriles, such as acetonitrile; and dimethylformamide or dimethylsulphone, but especially ethers and ether-like compounds, such as dialkyl ethers, dioxane, tetrahydrofurane or 1,2-dimethoxyethane; and also two-phase mixtures, such as water/benzene. Bases which may be mentioned are, in particular, tertiary amines, for example trialkylamines, pyridine or pyridine bases, but also NaH or, in the case of mixtures which contain water, alkali metal hydroxides or carbonates or alkaline earth metal hydroxides or carbonates.

The amides of the formula II, which are used as starting materials, can be manufactures as follows: an amide of the formula IV

(IV)

is allowed to react with a hexahydro-s-triazine of the formula V

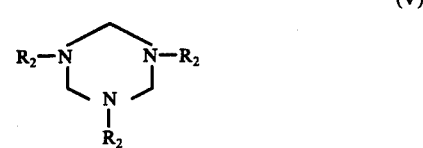
(V)

in the presence of an anhydrous organic or inorganic acid (for example HCl) at temperatures between $-40°$ C and $+30°$ C in an organic solvent which is liquid and inert under the reaction conditions, aminomethylation taking place. The substituents $R_1$ and $R_2$ have the meanings indicated under formula I. The intermediate products which are obtained as salts of the acid employed are converted into the free amides of the formula II by treatment with bases.

According to another method, which is described in Chem. Pharm. Bull 21, (12) page 2775-2778 [1973], compounds of the formula II are also obtainable by reacting compounds of the formula IV simultaneously with formaldehyde and the amine hydrochloride $R_2-NH_2 \cdot HCl$ in aqueous alcohol solution. In this case also the intermediate products of the formula II are obtained as salts (hydrochlorides) and are converted into the free amides by adding bases.

As shown in Example 3, the compounds of the formula I can advantageously be manufactured direct from the amides of the formula IV in a one-pot process by reacting these amides with a hexahydro-s-triazine of the formula V in the presence of an anhydrous acid in an inert organic solvent and then, without isolating the intermediate product of the formula II, carrying out the cyclisation with a compound of the formula III in the presence of a base. This particular embodiment of the process for the manufacture of the compounds of the formula I surprisingly has the advantage that even those compounds of the formula II in which $R_1$ represents a heterocyclic radical which itself is sensitive to alkali or which is rendered sensitive to alkali by a substituent can be cyclised without difficulty.

If they possess a ring nitrogen atom in the radical $R_1$ or a sulphur atom or the SO group in a substituent of $R_1$, compounds of the formula I manufactured by the process described can optionally be converted, in an additional operation, into their oxides, such as N-oxides, sulphoxides or sulphones, by means of a suitable oxidising agent, for example a per-acid. Furthermore, if they contain, in the radical $R_1$, a ring nitrogen atom which can be quaternized, compounds of the formula I can optionally be converted into their quaternary salts by means of suitable quaternising agents.

The examples which follow illustrate the process according to the invention. The temperatures are quoted in degrees centigrade.

EXAMPLE 1

A suspension of 50.6 g of N-(methylaminomethyl)-pyrazinamide hydrochloride in 500 ml of water is neutralized at 0° to 25° with 125 ml of 2 N sodium hydroxide solution. The mixture is now extracted with ethyl acetate, the organic phase is dried over magnesium sulphate and the solvent is evaporated. The residue is taken up in 300 ml of tetrahydrofurane and 24.8 g of phosgene in 300 ml of tetrahydrofurane are added dropwise. The addition takes place at 0° to 25° in the course of 1 hour. Thereafter 39.5 g of pyridine, dissolved in 100 ml of tetrahydrofurane, are added at room temperature in the course of a further hour. The reaction mixture is stirred for a further 2 hours and then heated under reflux for 3 hours. After cooling, the precipitate which has formed is filtered off, the filtrate is evaporated to dryness and the residue is taken up in chloroform, washed first with sodium bicarbonate solution and then with water and dried. The solvent is evaporated and the residue is recrystallized from ethyl acetate/n-hexane and 6-pyrazino-3-methyl-3,4-dihydro-2H-1,3,5-oxadiazin-2-one, which has a melting point of 151° to 152° C, is obtained.

EXAMPLE 2

A suspension of 19 g N-(methylaminomethyl)-picolinamide bis-hydrochloride in 400 ml of ethyl acetate is treated with excess concentrated sodium hydroxide solution, whilst cooling with ice, and the free base, which is present in the organic phase, is separated off rapidly, dried and freed from solvent. The free base is dissolved in 120 ml of dimethoxyethane and added dropwise, at 0° to +5°, in the course of 1 hour to a solution of 10 g of phosgene in 120 ml of dimethoxyethane. The temperature is then allowed to rise to 25° and a solution of 7.6 g of pyridine in 120 ml of dimethoxyethane is added dropwise in the course of 1 hour and the mixture is stirred for a further 2 hours at room temperature. Any precipitate which has formed is then filtered off, the filtrate is evaporated and the residue is taken up in a mixture of 500 ml of ethyl acetate and 20 ml of water. The aqueous phase is extracted with two further 50 ml portions of ethyl acetate. A brown oil, which can be crystallized by treatment with benzene and hexane, is obtained from the combined ethyl acetate extracts by concentrating.

The crystalline produce is N'-(chlorocarbonyl)-N'-methylaminomethyl-picolinamide and melts at 89°–91° C.

In order to carry out the cyclization, a suspension of 0.78 g of NaH in 40 ml of dimethoxyethane is prepared from a commercially available dispersion of NaH in oil by washing with benzene and dimethoxyethane. 5.4 g of the intermediate product (melting point 89°–91° C) described above, dissolved in 40 ml of dimethoxyethane, are added dropwise to this suspension at room temperature in the course of 20 minutes. The reaction is initially slightly exothermic. When the dropwise addition is complete, the temperature is slowly raised to +60° C and the mixture is stirred at this temperature for about a further 5 hours. The mixture is then allowed to cool and is poured onto a mixture of sodium acetate and ice and extracted with chloroform. The chloroform extract is evaporated and the residue is recrystallized from ethyl acetate/hexane. The produce is 6-(2-pyridinyl)-3-methyl-3,4-dihydro-2H-1,3,5-oxadiazin-2-one. It melts at 174°–177° C.

EXAMPLE 3

3.8 g = 0.105 mol of HCl gas are passed into 150 ml of dry dimethoxyethane. This solution is cooled to −35° C and 4.3 g = 0.033 mol of trimethyl-hexahydro-triazine are added dropwise. 19.1 g = 0.1 mol of finely powdered and very dry 2,6-dichloro-nicotinamide are then added to the solution, which has been cooled to −30° C. The amide is added while stirring vigorously. The mixture is stirred for about a further 1 hour at −30° C and the temperature of the mixture is then allowed to rise overnight to room temperature.

The mixture is then cooled again to −35° C and 100 ml of dry dimethoxyethane, a solution of 11.9 g = 0.12 mol of phosgene in 60 ml of toluene and a solution of 14.4 ml of dry pyridine in 20 ml of dimethoxyethane are added successively at −35° C, the two latter solutions being added dropwise and while stirring vigorously. The mixture is then stirred for about a further 1 hour at −30° C and the temperature is then allowed to rise to 0° C in the course of about 2 hours. A further 26 ml = 0.33 mol of pyridine are then added dropwise (whilst stirring). After 1 hour the temperature is allowed to rise slowly to room temperature and the stirrer is then switched off. The mixture is now heated to the reflux temperature and boiled for 15 hours. It is then allowed to cool and the liquid phase is decanted off from the oily precipitate and the solvent is completely removed. The residue is taken up in a mixture of water and ethyl acetate. The aqueous phase is extracted twice more with ethyl acetate and is then discarded. The combined ethyl acetate extracts are evaporated. Pure 6-(2,6-dichloro-3-pyridinyl)-3-methyl-3,4-dihydro-2H-1,3,5-oxadiazin-2-one, which has a melting point of 126°–128° C, is obtained therefrom by column chromatography on silica gel.

EXAMPLE 4

28.7 g = 0.15 mol of 6-(4'-pyridinyl)-3-methyl-3,4-dihydro-2H-1,3,5-oxadiazin-2-one are dissolved in 150 ml of chloroform, the solution is cooled to 0° C and a solution of 25.8 g of metachloroperbenzoic acid in 180 ml of chloroform is then added dropwise. When the dropwise addition is complete, the temperature is allowed to rise to 23° C in the course of 6 hours and the mixture is stirred at this temperature for a further 48 hours. After this time, the mixture should contain no further per-acid. The solvent is then evaporated and the residue is recrystallized from methanol. The product is 6-(4'-pyridinyl)-3-methyl-3,4-dihydro-2H-1,3,5-oxadiazin-2-one-1'-oxide. It melts at 246°–247° C.

EXAMPLE 5

2.37 g = 10 mmols of 6-(6'-methylthio-3'-pyridinyl)-3-methyl-3,4-dihydro-2H-1,3,5-oxadiazin-2-one are dissolved in 200 ml of chloroform and the solution is cooled to 0° C. 1.72 g = 10 mmols of metachloroperbenzoic acid, dissolved in 50 ml of chloroform, are then added dropwise in the course of 4 hours and the mixture is stirred for a further 4 hours. The temperature is then allowed to rise to 22° C and the mixture is stirred for a further 15 hours. After this time has elapsed no further peroxide should be detectable. The reaction mixture is then evaporated and the residue is recrystallized from ethyl acetate. The 6-(6'-methylsulphinyl-3'-pyridinyl)-3-methyl-3,4-dihydro-2-H-1,3,5-oxadiazin-2-one which is thus obtained melts at 197°–199° C.

EXAMPLE 6

1 g of 6-(4'-pyridinyl)-3-methyl-3,4-dihydro-2H-1,3,5-oxadiazin-2-one is dissolved in 12 ml of acetonitrile. 2 g of methyl iodide are added to this solution and the initially clear solution is allowed to stand overnight at room temperature. The thick slurry which forms during this time is filtered off and the crystals are washed well with ethyl acetate. The salt thus obtained melts at 198°–199° with decomposition. It is 6-(1'-methyl-4'-pyridinylonium)-3-methyl-3,4-dihydro-2H-1,3,5-oxadiazin-2-one iodide.

The following compounds were manufactured analogously to those in the preceding examples:

$$R_1-C(=N)-O-C(=O)-N(R_2)-CH_2-$$ (ring structure)

| $R_2$ | $R_1$ | Melting point in ° C |
|---|---|---|
| $CH_3$ | 4-pyridinyl | 163–164 |
| $CH_3$ | 3-pyridinyl | 138–140 |
| $CH_3$ | 2-pyridinyl | 174–177 |
| $CH_3$ | 2-thienyl | 204–205 |
| $CH_3$ | 2-furanyl | 157–158 |
| $CH_3$ | 2-(5-nitro-furanyl) | 211–213 |
| $CH_3$ | 2-(5-methyl-thienyl) | 136–137 |
| $CH_3$ | 2-(1-methyl-pyrrolyl) | 178–181 |
| $CH_3$ | 2-quinolinyl | 157–159 |
| $CH_3$ | 3-(2-chloro-pyridinyl) | 80–82 |
| $CH_3$ | 3-(6-chloro-pyridinyl) | 222–224 |
| $CH_3$ | 4-(2-phenyl-quinolinyl) | |
| $CH_3$ | 5-(2,4-bis-diethylamino-pyrimidinyl) | |
| $CH_3$ | 6-(2,4-bis-diethylamino-pyrimidinyl) | |
| $CH_3$ | 2-benzofuranyl | 256–258 |
| $CH_3$ | 4-pyridinyl-N-oxide | 246–247 |
| $CH_3$ | 4-(1-methyl-pyridinium iodide) | 198–199 |
| $CH_3$ | 3-pyridinyl-N-oxide | 195–199 |
| $CH_3$ | 3-(1-methyl-pyridinium iodide) | 194–197 |
| $CH_3$ | 3-(6-[4-morpholinyl]-pyridinyl) | 197–200 |
| $CH_3$ | 4-(2,6-dichloro-pyridinyl) | 141–143 |
| $CH_3$ | 3-(2,6-dichloro-pyridinyl) | 126–128 |
| $CH_3$ | 3-(6-methylthio-pyridinyl) | 184–187 |
| $CH_3$ | 3-(5-nitro-6-methylthio-pyridinyl) | 219–220 |
| $CH_3$ | 2-benzoxazolyl | 251–253 |
| $CH_3$ | 3-(6-methylsulphonyl-pyridinyl) | 225–227 |
| $CH_3$ | 3-(6-methylsulphinyl-pyridinyl) | 197–199 |
| $CH_3$ | 2-(5-nitro-benzofuranyl) | |
| $CH_3$ | 2-(6-nitro-benzofuranyl) | |
| $CH_3$ | 4-quinolinyl | |
| $CH_3$ | 5-(2-chloro-4-diethylamino-pyrimidinyl) | |
| $CH_3$ | 6-(2-chloro-4-diethylamino-pyrimidinyl) | |
| $CH_3$ | 3-(2,4-dinitro-thienyl) | |
| $CH_3$ | 4-(2-methyl-5-cyano-6-chloro-pyridinyl) | |
| $CH_3$ | 4-(2-ethoxycarbonyl-pyridinyl) | |
| $CH_3$ | 3-(5-methoxycarbonyl-pyridinyl) | |
| $CH_3$ | 2-(6-methoxycarbonyl-pyridinyl) | |
| $CH_3$ | 2-(1-methyl-indolyl) | |
| $CH_3$ | 2-(3-nitro-thienyl) | |
| $CH_3$ | 3-(2-nitro-thienyl) | |
| $CH_3$ | 2-thiazolyl | |
| $CH_3$ | 5-(1-methyl-4-nitro-imidazolyl) | |
| $CH_3$ | 5-(2-methyl-6-chloro-pyrimidinyl) | |
| $CH_3$ | 5-(2-methoxy-pyridinyl) | 159–161 |
| $CH_3$ | 6-(2,4-dimethoxy-pyrimidinyl) | |
| $CH_3$ | 6-(2,4-dimethoxy-pyridinyl) | |
| $CH_3$ | 3-(1-methyl-indolyl) | |
| $CH_3$ | 4-thiazolyl | |
| $CH_3$ | 4-(2-dimethylaminocarbonyl-pyridinyl) | |
| $CH_3$ | 5-(2-trifluoromethyl-imidazolyl) | |
| $CH_3$ | 5-(1-methyl-4-cyano-imidazolyl) | |
| $CH_3$ | 3-(2-methyl-6-chloro-pyridinyl) | |
| $CH_3$ | 3-(2-methyl-6-methoxy-pyridinyl) | |
| $CH_3$ | 3-(2-methyl-6-methylthio-pyridinyl) | |

-continued $$R_1 \underset{N}{\overset{O}{\bigcirc}} \underset{N-R_2}{\overset{O}{\bigcirc}}$$

| R₂ | R₁ | Melting point in °C |
|---|---|---|
| CH₃ | 3-(5-nitro-6-methoxy-pyridinyl) | |
| CH₃ | 3-(5-nitro-6-chloro-pyridinyl) | |
| CH₃ | 3-(5-nitro-6-cyano-pyridinyl) | |
| CH₃ | 3-(6-chloro-2-methylthio-pyridinyl) | |
| CH₃ | 4-(2,3,5,6-tetrachloro-pyridinyl) | |
| CH₃ | 3-(6-dimethylamino-pyridinyl) | |
| CH₃ | 3-(6-trimethylammonium-pyridinyl) chloride | |
| CH₃ | 3-(6-cyano-pyridinyl) | |
| CH₃ | 5-(1-benzyl-4-cyano-imidazolyl) | |
| CH₃ | 2-benzimidazolyl | |
| CH₃ | 6-(6-bromo-3-pyridinyl) | |
| CH₃ | 6-(2,6-dibromo-3-pyridinyl) | |
| CH₃ | 6-(2,4-dimethoxy-5-nitro-pyrimidinyl) | |
| CH₃ | 3-coumarinyl | |
| CH₃ | 6-(2,4-bis-dimethylamino-s-triazinyl) | |
| CH₃ | 6-(2-dimethylamino-4-methoxy-5-triazinyl) | |
| CH₃ | 4-(2,3,5-trichloro-6-methoxy-pyridinyl) | |
| CH₃ | 2-(3-chloro-6-nitro-benzothienyl) | |
| CH₃ | 2-(3,6-dichloro-benzothienyl) | |
| CH₃ | 2-(3-chloro-benzothienyl) | |
| CH₃ | 5-(1,3-dimethyl-4-nitro-pyrazolyl) | |
| CH₃ | 3-(2-methoxy-4-methoxymethyl-5-nitro-pyridinyl) | |
| CH₃ | 2-(1-methyl-5-nitro-benzimidazolyl) | |
| CH₃ | 2-(1-methyl-5-nitro-imidazolyl) | |
| CH₃ | 6-(2,4-dimethoxy-5-nitro-pyrimidinyl) | |
| CH₃ | 3-(2-methoxy-4,6-dimethyl-pyridinyl) | |
| CH₃ | 5-(1-methyl-4-nitro-imidazolyl) | |
| CH₃ | 2-(3-benzoyl-quinoxalyl) | |
| CH₃ | 2-(3-[3',4'-dimethoxy-benzyl]-quinoxalyl) | |
| CH₃ | 2-(3-[2',5'-dimethoxy-benzyl]-quinoxalyl) | |
| CH₃ | 2-(3-[3',4',5'-trimethoxy-benzyl]-quinoxalyl) | |
| ▷—CH₂ | (3',[6'-chloro-pyridinyl-]) | 160–163 |
| ▷—CH₂ | (4'-pyridinyl) | 98–99 |
| C₂H₅ | (6'-chloro-3'-pyridinyl) | |
| (CH₃)₂CH | (6'-methoxy-3'pyridinyl) | |
| n-C₄H₉ | (2',6'-dichloro-3'-pyridinyl) | |
| CH₂=CH—CH₂ | (6'-methylthio-3'-pyridinyl) | |
| CH₃ | 3-(6'-fluoro-pyridinyl) | |
| CH₃ | 3-(2'-fluoro-6'-chloro-pyridinyl) | |

The new diazine derivatives of the formula I are employed in order to combat coccidiosis in poultry. Diazine derivatives which correspond to the formula Ia $$R_1 \underset{N}{\overset{O}{\bigcirc}} \underset{N-\text{lower alkyl}}{\overset{O}{\bigcirc}} \quad \text{(Ia)}$$

wherein $R_1$ has the meaning indicated under formula I and preferably represents an optionally substituted pyridine radical, have proved particularly effective.

Amongst the diseases which occur in poultry, coccidiosis is the most widespread disease. It is caused by protozoa of the genus Eimeria, such as, for example, *Eimeria tenella, Eimeria brunetti, Eimeria maxima, Eimeria necatrix, Eimeria acervulina* and the like. Animals infested with coccidia show a poor increase in weight, accompanied by haemorrhages in the intestines and elimination of blood in the excreta; in the case of severe infestation, coccidiosis leads to a high death rate in poultry. Commercially available compounds having a coccidiostatic action are known to lead to the development of resistance in the parasites within a short time. Therefore, it is extremely important for poultry rearing that new compounds are developed which are suitable for combating and preventing this disease.

The coccidiostatic action of the diazine derivatives of the formula I is illustrated in the experiment which follows:

Experiments on hens infested with *Eimeria tenella*

10 8-day old chicks were infested with 80,000 sporulated oocysts of *Eimeria tenella*. Medicated chickfeed which contains 400 ppm of the active substance is administered ad libitum for 3 days before the infestation and for 10 days after the infestation. At the end of the experiment the chicks were dissected. 10 untreated chicks which were not infested and 10 infested untreated chicks were used as control. The amount of active substance taken in per group was determined by back-weighing the feed. The mortality, the increase in weight, the condition of the appendices and the discharge of oocysts compared with the two control groups were used as parameters of action.

The active compounds were tolerated by the chickens without producing any symptoms (no mortality); no oocysts were discharged and no lesions of the appendices were found.

In the case of the infested control animals the mortality was 20%; severe lesions of the appendices were found.

The coccidiostatic agents according to the invention are manufactured in a manner which is in itself known by intimately mixing and grinding active compounds of the formula I with suitable excipients, optionally with the addition of dispersing agents or solvents, which are inert towards the active compounds. The active compounds can be present, and employed, in the following formulations:

Solid formulations

Production of a premix;

Active compound concentrates which can be dispersed in water

Power mixture

Liquid formulations

Solutions and pastes (emulsions).

The particular size is appropriately up to about 0.1 mm for dusting agents and powder mixtures and 10 to 500μ (0.01 to 0.5 mm) for granules.

Coccidiostatic agents are preferably in the form of feed concentrates. In this case, for example, production rations, fodder grain or protein concentrates are used as the excipients. In addition to the active compounds, feed concentrates of this type can also contain additives, vitamins, antibiotics, chemotherapeutic agents or other pesticides, mainly bacteriostatic agents, fungistatic agents, anthelmintics, coccidiostatic agents or also hormone preparations, substances which have an anabolic action of other substances which promote the growth or influence the quality of the meat of animals for slaughter or which are useful for the organism in another way. The coccidiostatic agents according to the invention can, if their solubility in water permits, also by admixed to the drinking water used for the animals.

Feed concentrates

The following feed mixtures are used to produce 6,000 parts by weight of final feed containing (a) 25 ppm, (b) 50 ppm, (c) 200 ppm and (d) 400 ppm respectively: (a) 0.15 part by weight of a compound according to formula I, 48.85 parts by weight of Bolus alba and 150.0 parts by weight of a standard feed for poultry; (b) 0.30 parts by weight of a compound according to formula I, 44.70 parts by weight of Bolus alba, 5.0 parts by weight of silica and 150.0 parts by weight of a standard feed for poultry; (c) 1.2 parts by weight of a compound according to formula I, 43.8 parts by weight of Bolus alba, 5.0 parts by weight of silica and 150.0 parts by weight of a standard feed for poultry and (d) 2.4 parts by weight of a compound according to formula I, 47.6 parts by weight of Bolus alba and 150.0 parts by weight of a standard feed for poultry.

The active compounds are either mixed directly into the excipients or, for example, are dissolved in a suitable solvent and absorbed onto the excipients. Subsequently the mixture is ground to the desired particle size of, for example, 0.5 to 10 microns. The feed premixes are mixed with 5,800 parts by weight of standard feed. In addition, these feed premixes can be pelleted to give 6,000 parts by weight of final feed (feed pellets).

Other biocidal active compounds or agents can be admixed to the agents according to the invention, which have been described. Thus, in addition to the said compounds of the general formula I, the new agents can contain, for example, bactericides, bacteriostatic agents or nematicides in order to broaden the spectrum of action.

We claim:

1. A compound of the formula

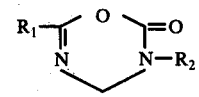

in which $R_1$ denotes a heterocyclic-aromatic radical selected from the group consisting of pyrazinyl, pyrrolyl, thiazolyl, imidazolyl, pyrimidinyl, furyl, thienyl, pyridinyl, quinolyl, indolyl, benzofuranyl and the quaternary ammonium salts and N-oxides of the N-containing heterocycles, which is optionally substituted by halogen, lower alkyl, aryl, nitro, cyano, trifluoromethyl, carboxyl, $R_3OOC-$, $(R_3)_2NCO-$, $(R_3)_2N-$, $R_3O-$, $R_3SO_2-$, $R_3SO-$ or $R_3S-$, and $R_2$ and $R_3$ independently of one another denote lower alkyl, alkoxyalkyl, alkenyl or cycloalkyl which is optionally bonded via a methylene or ethylene bridge.

2. The compound of claim 1 wherein $R_2$ is lower alkyl.

3. The compound of claim 1 wherein $R_1$ represents a pyridinyl radical which is optionally substituted by halogen, lower alkyl, aryl, nitro, cyano, trifluoromethyl, carboxyl, $R_3OOC-$, $(R_3)_2NCO-$, $(R_3)_2N-$, $R_3O-$, $R_3SO_2-$, $R_3SO-$ of $R_3S-$, $R_2$ denotes lower alkyl, and $R_3$ is lower alkyl, alkoxyalkyl, alkenyl or cycloalkyl which is optionally bonded via a methylene or ethylene bridge.

4. A coccidiostatic composition which comprises an effective coccidiostatic amount of a compound of claim 1 and a suitable carrier therefor.

5. A method for combatting coccidiosis in poultry which comprises applying to the locus infested therewith an effective coccidiostatic amount of a compound of claim 1.

6. The method of claim 5, wherein $R_2$ is lower alkyl.

7. The method of claim 5, wherein $R_1$ represents a pyridinyl radical which is optionally substituted by halogen, lower alkyl, aryl, nitro, cyano, trifluoromethyl, carboxyl, $R_3OOC-$, $(R_3)_2NCO-$, $(R_3)_2N-$, $R_3O-$, $R_3SO_2-$, $R_3SO-$ or $R_3S-$, $R_2$ is lower alkyl, and $R_3$ denotes lower alkyl, alkoxyalkyl, alkenyl or cycloalkyl which is optionally bonded via a methylene or ethylene bridge.

* * * * *